(12) United States Patent
Tsai et al.

(10) Patent No.: US 8,524,895 B2
(45) Date of Patent: *Sep. 3, 2013

(54) METHOD FOR PREPARING AMIDE

(75) Inventors: Tung-Han Tsai, Taipei (TW); Pin-To Yao, Taipei (TW); Cheng-Fa Hsieh, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 561 days.

This patent is subject to a terminal disclaimer.

(21) Appl. No.: 12/501,699

(22) Filed: Jul. 13, 2009

(65) Prior Publication Data

US 2010/0063274 A1      Mar. 11, 2010

(30) Foreign Application Priority Data

Sep. 11, 2008   (TW) ............................ 97134806 A

(51) Int. Cl.
*C07D 201/04*     (2006.01)
*C07D 223/10*     (2006.01)
(52) U.S. Cl.
USPC ........................................ 540/534; 540/484
(58) Field of Classification Search
USPC ................................. 540/534, 484
See application file for complete search history.

(56) References Cited

U.S. PATENT DOCUMENTS

| 5,225,547 A | 7/1993 | Izumi |
| 5,571,913 A | 11/1996 | Thomissen |
| 6,750,336 B2 * | 6/2004 | Sato et al. ................... 540/535 |

FOREIGN PATENT DOCUMENTS

WO   WO 2005/028446   *  3/2005

OTHER PUBLICATIONS

WO 2005/028446(English Translation), 2005.*

* cited by examiner

*Primary Examiner* — Shailendra Kumar
(74) *Attorney, Agent, or Firm* — Sughrue Mion, PLLC

(57) ABSTRACT

The present invention provides a method for preparing amides, in which an amino acid ionic liquid is used as both a reaction medium and a catalyst to catalyze Beckman rearrangement of a ketoxime, so as to produce an amide. In the method, the rearrangement is conducted by catalyzing a ketoxime with an amino acid ionic liquid having the asymmetric property at a moderate reaction temperature during a short reaction time, so as to produce an amide without adding other catalysts such as concentrate sulfuric acid. The method has advantages such as avoiding corrosion in equipments with pipelines, the high conversion rate of ketoximes and the high selectivity of amides.

16 Claims, No Drawings

METHOD FOR PREPARING AMIDE

BACKGROUND OF THE INVENTION

1. Field of the Invention

The present invention relates to methods for preparing amides, and more particularly, to a method for preparing amides by catalyzing ketoximes with ionic liquids.

2. Description of the Prior Art

In the recent years, ionic liquids are widely applied in the chemical field. From a practical aspect, ionic liquids are salts with melting points below 100° C., composed of anions and cations, and have special properties including a high polarity, a low vapor pressure, a low melting point, non-inflammability, resistance to strong acids, resistance to high temperatures, high electrical conductivity, an excellent electrochemical property, and a broader liquid temperature range (−96° C. to 400° C.), and thus can be applied in various technologies such as chemical synthesis, catalysis, electrochemistry, analytical chemistry and separation technologies. Because ionic liquids can be used under a normal pressure, they can replace commonly used volatile organic compounds (VOC), so as to reduce contamination of VOC to the environment and avoid exposure of VOC to operators. Further, ionic liquids are recyclable. Hence, ionic liquids are considered as a new green solvent.

Currently, a lot of research works focus on introducing atoms having specific functions or reactivity into the molecular structures of ionic liquids at room temperature to prepare functionalized ionic liquids and give ionic liquids certain special properties, applications or functions, so that they become "task specific ionic liquids". For example, an ionic liquid having amino at the terminal of a cationic substituent captures carbon dioxide at room temperature and releases it at a higher temperature, and thus can selectively separate carbon dioxide from a mixed gas (J. Am. Chem. Soc., 2002, 124, 927).

Caprolactam is an important raw material in the manufacture of nylon 6 fibers and thin films. Beckman rearrangement of cyclohexanone oxime is an important reaction step in producing caprolactam. Currently, fuming sulfuric acid is used as a catalyst for converting cyclohexanone oxime to caprolactam sulfate during Beckman rearrangement, and then ammonia is used for neutralization, so as to obtain caprolactam. While the conversion rate of cyclohexanone oxime is almost 100% and the selectivity for caprolactam is 99%, a large amount of low-valued ammonium sulfate is generated during the reaction, and concentrated sulfuric acid used for catalysis causes problems such as corrosion to the whole equipment and environmental pollution. In the recent years, researches on new production technologies of caprolactam focus on reducing or avoiding the generation of the by-product, ammonium sulfate. Moreover, compared with the gas phase reaction, liquid-phase rearrangement has advantages including moderate reaction conditions, fewer requirements to the equipments, etc., and is advantageous to the reconstruction of the current equipments. As a result, scholars worldwide have put efforts on developing liquid-phase rearrangement, and attained substantial developments and breakthrough. For example, in U.S. Pat. No. 5,225,547 assigned to Sumitomo Chemical Company Ltd. in Japan, a catalytic system consisting of an alkylating agent and N,N-dimethylformamide (DMF) is used to give the selectivity of caprolactam up to 99.8%. In U.S. Pat. No. 5,571,913 assigned to DSM N.V. in Holland, a cation exchange resin is used as a catalyst to give the selectivity of caprolactam up to 100%.

Accordingly, there is an urgent need of a method for preparing amides by liquid-phase rearrangement of ketoximes without corrosive catalysts.

SUMMARY OF THE INVENTION

In view of the foregoing problems, the present invention provides a method for preparing amides by catalyzing the rearrangement with ionic liquids.

The present invention further provides a method for preparing amides without generating volatiles or corroding equipments with pipelines.

In addition, the present invention provides a method for preparing amides without generating the by-product, ammonium sulfate.

Therefore, the present invention provides a method for preparing amides, which comprises the step of catalyzing the Beckman rearrangement of a ketoxime to produce an amide in the presence of a catalyst including a N-substituted amino acid ionic liquid having a cation represented by the following formula (I) and one or more anions selected from the group consisting of inorganic acid ions, organic acid ions and a combination thereof:

wherein $R_1$ is hydrogen, cycloimino or $C_1$-$C_8$alkyl, in which $C_1$-$C_8$alkyl is unsubstituted or substituted by a substituent selected from hydroxyl (—OH), carboxyl (—COOH), guanidino (NH$_2$C(=NH)NH—), amino (—NH$_2$), amido (RCONH—), hydroxyphenyl, $C_1$-$C_8$alkylthio, thiol (—SH), $C_6$-$C_{10}$aryl and 5- to 10-membered heteroaryl; and $R_2$ and $R_3$ are independently hydrogen or $C_1$-$C_8$alkyl, wherein $C_1$-$C_8$alkyl is unsubstituted or substituted by a substituent selected from carboxyl (—COOH), sulfo (—SO$_3$H), chlorosulfinyl (ClSO—) and ester group (—COOR, wherein R is $C_1$-$C_8$alkyl), oxo (=O) and $C_6$-$C_{10}$aryl, provided that $R_2$ and $R_3$ are not hydrogen concurrently; wherein the numbers of anions and cations are such that N-substituted amino acid ionic liquids are electroneutral.

Compared with conventional processes for catalyzing the Beckman rearrangement by using fuming sulfuric acid, the method of the present invention for preparing amides uses neutral ionic liquids to catalyze the reaction without generating volatiles, corroding equipments with pipelines, producing by-product, ammonium sulfate, and other cocatalysts. Therefore, the method of the present invention is suitable for mass production in industry.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention discloses a method for preparing amides, which comprises the step of catalyzing the Beckman rearrangement of a ketoxime to produce an amide in the presence of a catalyst including a N-substituted amino acid ionic liquid having a cation represented by the following formula (I) and one or more anions selected from the group consisting of inorganic acid ions, organic acid ions and a combination thereof:

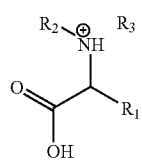

(I)

wherein $R_1$ is hydrogen, cycloimino, or $C_1$-$C_8$alkyl, wherein $C_1$-$C_8$alkyl is unsubstituted or substituted by a substituent selected from hydroxyl (—OH), carboxyl (—COOH), guanidino (NH$_2$C(=NH)NH—), amino (—NH$_2$), amido (RCONH—), hydroxyphenyl, $C_1$-$C_8$alkylthio, thiol (—SH), $C_6$-$C_{10}$aryl and 5- to 10-membered heteroaryl; and $R_2$ and $R_3$ are independently hydrogen or $C_1$-$C_8$alkyl, wherein $C_1$-$C_8$alkyl is unsubstituted or substituted by a substituent selected from carboxyl (—COOH), sulfo (—SO$_3$H), chlorosulfinyl (ClSO—), ester group (—COOR, wherein R is $C_1$-$C_8$alkyl), oxo (=O) and $C_6$-$C_{10}$aryl, provided that $R_2$ and $R_3$ are not hydrogen concurrently; wherein the numbers of anions and cations are such that N-substituted amino acid ionic liquids are electroneutral.

Generally speaking, the molar ratio of amino acid ionic liquid to ketoxime is in a range from 1:10 to 10:1, and preferably in a range from 1:5 to 5:1. The reaction is performed at a temperature from 60° C. to 150° C., and preferably from 90° C. to 130° C., and the reaction is performed for 0.1 to 10 hours, and preferably 0.5 to 3 hours.

In a preferred embodiment, $R_1$ is $C_1$-$C_8$alkyl substituted by carboxyl (—COOH), guanidino (NH$_2$C(=NH)NH—), amino (—NH$_2$), amido (RCONH—) or hydroxyphenyl, and $R_2$ and $R_3$ are independently ($C_1$-$C_8$)alkyl.

The term "$C_1$-$C_8$alkyl" used herein refers to straight, branched, or cyclic alkyl. The $C_1$-$C_8$alkyl can be, but not limited to, methyl, ethyl, propyl, isopropyl, butyl, sec-butyl, pentyl, hexyl and cyclohexyl, wherein methyl, ethyl, propyl, butyl and pentyl are preferable.

In the present invention, an anion is selected from the group consisting of sulfate, methylsulfonato, trifluoroacetato, hexafluorophosphato, fluoroborate and a combination thereof, wherein sulfate is more preferable.

In a preferred embodiment of the present invention, the N-substituted amino acid ionic liquid is an amino acid sulfuric acid-ionic liquid selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof. Preferably, the N-substituted amino acid ionic liquid is an isoleucine sulfuric acid-ionic liquid, N,N-dimethylglutamic acid sulfate, N,N-dimethylaspartic acid sulfate, N-methylglutamic acid sulfate or N-methylaspartic acid sulfate. It is known from the above that one or more amino acid ionic liquids can be used in the method of the present invention.

Furthermore, the ketoxime used for preparing the amide in the present invention is selected from acetone oxime, butanone oxime, benzophenone oxime, acetophenone oxime, cyclopentanone oxime, cyclohexanone oxime, cycloheptanone oxime, cyclooctanone oxime and cyclododecanone oxime.

In one embodiment of the present invention, the N-substituted amino acid ionic liquid is N,N-dimethylglutamic acid sulfuric acid-ionic acid, and the ketoxime is cyclohexanone oxime.

The present invention further discloses a method for preparing the above-mentioned N-substituted amino acid ionic liquid, which comprises the steps of reacting an amino acid represented by the following formula (II) with $C_1$-$C_8$aldehyde unsubstituted or substituted by a substituent selected from the group consisting of carboxyl (—COOH), sulfo (—SO$_3$H), chlorosulfinyl (ClSO—), ester group (—COOR, wherein R is $C_1$-$C_8$alkyl), oxo (=O) and $C_6$-$C_{10}$aryl to form a N-substituted amino acid, and then reacting the N-substituted amino acid with an acid to form the above-mentioned N-substituted amino acid ionic liquid:

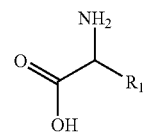

(II)

wherein $R_1$ is hydrogen, cycloimino, or $C_1$-$C_8$alkyl, wherein $C_1$-$C_8$alkyl is unsubstituted or substituted by a substituent selected from hydroxyl (—OH), carboxyl (—COOH), guanidino (NH$_2$C(=NH)NH—), amino (—NH$_2$), amido (RCONH—), hydroxyphenyl, $C_1$-$C_8$alkylthio, thiol (—SH), $C_6$-$C_{10}$aryl and 5- to 10-membered heteroaryl.

In the method of producing the above-mentioned N-substituted amino acid ionic liquids of the present invention, the amino acid represented by the formula (II) can be L-amino acid, D-amino acid or DL-amino acid, such as, but not limited to, glycine (i.e. $R_1$=H), isoleucine (i.e. $R_1$=isobutyl), arginine (i.e. $R_1$=guanidinopropyl), glutamic acid (i.e. $R_1$=carboxylethyl), tyrosine (i.e. $R_1$=hydroxybenzyl), aspartic acid (i.e. $R_1$=hydroxymethyl), lysine (i.e. $R_1$=aminobutyl), threonine (i.e. $R_1$=hydroxyethyl), phenylalanine (i.e. $R_1$=benzyl) and serine (i.e. $R_1$=hydroxymethyl). In the method of the present invention, aldehydes are preferably unsubstituted $C_1$-$C_8$aldehydes. More preferably, the aldehydes can be, but not limited to, formaldehyde, acetaldehyde, propionaldehyde, butyraldehyde and valeraldehyde.

Usually, amino acids react with unsubstituted $C_1$-$C_8$aldehydes in the presence of a Pd/C catalyst under the hydrogen atmosphere to form N,N-di($C_1$-$C_8$alkyl) amino acid. In another preferred embodiment of the present invention, amino acids react with unsubstituted $C_1$-$C_8$aldehydes, and then the reduction is conducted in the presence of a Pd/C catalyst under the hydrogen atmosphere to form N-mono($C_1$-$C_8$alkyl) amino acids.

SYNTHETIC EXAMPLE 1

Synthesis of N,N-dimethylaspartic Acid Sulfate Ionic Liquid 25 g of aspartic acid was placed in a 500 ml round-bottom flask, 60 ml of formaldehyde aqueous solution (concentration: 37%), 200 ml of water and 8 g of Pd/C were added sequentially. The air in the flask was displaced by hydrogen, the flask was placed under the hydrogen atmosphere and the reaction was conducted for 48 hours. After the reaction, the remaining hydrogen was displaced by nitrogen, the flask was heated to 90° C. under reflux, and Pd/C was filtered out at the high temperature to obtain a colorless aqueous solution. The colorless aqueous solution was concentrated and azeotroped with 100 ml of toluene to further remove the water. The product was dried under high vacuum, and ground by using a spatula to obtain 28.92 g of N,N-dimethylaspartic acid as a pale yellow solid (Yield: 95.54%).

10 g of dimethylaspartic acid was placed in a 250 ml round-bottom flask, and 40 ml of water was added and stirred for 30 minutes. Then, 7.36 g of concentrated sulfuric acid (concentration: 98%) was slowly added to the flask. After the addition, a reaction was conducted for 2 hours. The reaction solution was concentrated, and azeotroped with 100 ml of toluene to further remove the water. Afterwards, the product was dried under high vacuum, and ground by using a spatula to obtain 15.34 g of N,N-dimethylaspartic acid sulfate as tawny oil (Yield: 95.33%).

SYNTHETIC EXAMPLE 2

Synthesis of N-methylglutamic Acid Sulfate Ionic Liquid 10 g of glutamic acid was added to a 250 ml round-bottom flask, and 100 ml of water was added and stirred for 30 minutes. Then, a formaldehyde aqueous solution (concentration: 37%, 20 ml) was added to the flask, and the reaction was conducted at 80° C. After performing the reaction for 3 hours, a yellow liquid was obtained. The liquid was concentrated, and azeotroped with 100 ml of toluene to further remove the water. The product was dried under high vacuum to obtain a yellow solid (10.52 g, Yield: 97.22%).

100 ml of water and 10.3 g of the above yellow solid (unsaturated intermediate) was added to the flask, and 5 g of Pd/C (10%) was further added. The air in the flask was displaced by hydrogen, and a reduction was performed under hydrogen for 24 hours. After the reaction, hydrogen was displaced by nitrogen, and the flask was heated to 80° C. Pd/C was filtered out at the high temperature, and the filtrate was collected. The filtrate was concentrated, and azeotroped with 100 ml of toluene to further remove the water. The product was dried under vacuum to obtain 10.65 g of N-methylglutamic acid as a solid (Yield: 99.1%).

10.65 g of N-methylglutamic acid was placed in a 250 ml round-bottom flask, and 100 ml of water was added to the flask and stirred by using a magnetic stirrer for 30 minutes. Then, 6.38 g of concentrated sulfuric acid (concentration: 98%) was slowly dropped into the flask under stirring, and stirred for additional 2 hours after dropping. After the reaction, the reaction solution was concentrated, azeotroped with toluene to further remove the water and dried under vacuum to obtain 16.5 g of N-methylglutamic acid sulfate as yellow oil (Yield: 97.7%).

SYNTHETIC EXAMPLE 3

Synthesis of N-methylaspartic Acid Sulfate Ionic Liquid 10 g of aspartic acid was added to a 250 ml round-bottom flask, and 100 ml was added and stirred for 30 minutes. A formaldehyde aqueous solution (concentration: 37%, 20 ml) was added to the flask, and the reaction was conducted at 80° C. After performing the reaction for 3 hours, a yellow liquid was obtained. The yellow liquid was concentrated, azeotroped with 100 ml of toluene to further remove the water and dried under vacuum to obtain a yellow solid (10.63 g, Yield: 97.52%).

100 ml of water, 10.5 g of the above yellow solid and 5 g of Pd/C (10%) were added sequentially to the flask. The air in the flask was replaced by hydrogen, and a reduction was performed under hydrogen in the flask for 24 hours. After the reaction, hydrogen was displaced by nitrogen, and the flask was heated to 80° C. Pd/C was filtered out at the high temperature, and the filtrate was collected. The filtrate was concentrated, azeotroped with 100 ml of toluene to further remove the water and dried under vacuum to obtain 10.7 g of N-methylaspartic acid as a solid (Yield: 99.2%).

10.7 g of N-methylaspartic acid was placed in a 250 ml round-bottom flask, and 100 ml of water was added to the flask and stirred for 30 minutes by using a magnetic stirrer. 7.12 g of concentrate sulfuric acid (concentration: 98%) was slowly dropped into the flask under stirring, and stirred for additional 2 hours after dropping. After the reaction, the reaction solution was concentrated, azeotroped with 100 ml of toluene to further remove the water and dried under vacuum to obtain 17 g of N-methylaspartic acid sulfate as yellow oil (Yield: 95.3%).

SYNTHETIC EXAMPLE 4

Synthesis of N,N-dimethylglutamic Acid Sulfate Ionic Liquid 25 g of glutamic acid was placed in a 500 ml round-bottom flask, a formaldehyde aqueous solution (concentration: 37%, 60 ml), 200 ml of water and 8 g of Pd/C were added sequentially. The air in the flask was displaced by hydrogen, the flask was placed under the hydrogen atmosphere and the reaction was conducted for 48 hours. After the reaction, the remaining hydrogen was displaced by nitrogen and the flask was heated to 90° C. under reflux. Pd/C was filtered out at the high temperature to obtain a colorless aqueous solution. The colorless aqueous solution was concentrated, and azeotroped with 100 ml of toluene to further remove the water. The product was dried under high vacuum to obtain 29 g of N,N-dimethylglutamic acid as a pale yellow solid (Yield: 97.3%).

4.9 g of dimethylglutamic acid was placed in a 100 ml round-bottom flask, and 40 ml of water was added and stirred for 30 minutes. Then, 2.98 g of concentrated sulfuric acid (concentration: 98%) was slowly added to the flask. After the addition, a reaction was conducted for 2 hours. The reaction solution was concentrated, and azeotroped with 100 ml of toluene to further remove the water. Afterwards, the product was dried under high vacuum to obtain 7.6 g of N,N-dimethylglutamic acid sulfate as tawny oil (Yield: 96.32%).

The other types of ionic liquids can also be prepared according to the aforesaid methods, and therefore the following Examples are provided to further illustrate the methods of the present invention for preparing amides.

EXAMPLES 1-4

In Examples 1-4, according to Table 1, a toluene solvent (50 ml) and 0.01 mole of the amino acid ionic liquid were added to a 250 ml three-necked round-bottom flask, and stirred by a magnetic stirrer and heated to 130° C. A predetermined amount of ketoxime was added, wherein the molar ratio of the ionic liquid to the ketoxime was 5/1. After the reaction was performed for 3 hours, the conversion rate of the reactant and the selectivity of the product were measured by gas chromatography. The results are shown in Table 1.

Conversation rate of the ketoxime and the selectivity of the amides are calculated by the following equations:

$$\text{Conversion rate (\%)} = [\text{mole number of reacted ketoxime/mole number of original ketoxime (\%)}] \times 100\%$$

$$\text{Selectivity (\%)} = [\text{mole number of the resulting amide/mole number of reacted ketoxime (\%)}] \times 100\%$$

TABLE 1

| Example | Ionic Liquid | Ketoxime | Molar Ratio of Ionic Liquid/ Ketoxime | Reaction Temperature (° C.) | Reaction Time (h) | Amide | Conversion Rate | Selectivity |
| --- | --- | --- | --- | --- | --- | --- | --- | --- |
| 1 | Isoleucine Sulfuric Acid-Ionic Liquid | Cyclohexanone Oxime | 5/1 | 130 | 3 | Caprolactam | 99% | 84.3% |
| 2 | Aspartic Acid Sulfuric Acid-Ionic Liquid | Cyclohexanone Oxime | 5/1 | 130 | 3 | Caprolactam | 85.9% | 63.1% |
| 3 | Threonine Sulfuric Acid-Ionic Liquid | Cyclohexanone Oxime | 5/1 | 130 | 3 | Caprolactam | 23.9% | 65.6% |
| 4 | Glycine Sulfuric Acid-Ionic Liquid | Cyclohexanone Oxime | 5/1 | 130 | 3 | Caprolactam | 91.4% | 82.4% |

EXAMPLES 5-7

In Examples 5-7, according to Table 2, a toluene solvent (50 ml) and 0.01 mole of the amino acid ionic liquid were added to a 250 ml three-necked round-bottom flask, stirred by a magnetic stirrer and heated to 110° C. A predetermined amount of ketoxime was added, wherein the molar ratio of the ionic liquid to ketoxime was 5/1. After the reaction was performed for 2 hours, the conversion rate of the reactant and the selectivity of the product were measured by gas chromatography. The results are shown in Table 2.

TABLE 2

| Example | Ionic Liquid | Ketoxime | Molar Ratio of Ionic Liquid/ Ketoxime | Reaction Temperature (° C.) | Reaction Time (h) | Amide | Conversion Rate | Selectivity |
| --- | --- | --- | --- | --- | --- | --- | --- | --- |
| 5 | Aspartic Acid Sulfuric Acid-Ionic Liquid | Cyclohexanone Oxime | 5/1 | 110 | 2 | Caprolactam | 99.7% | 84.8% |
| 6 | N-Methylaspartic Acid Sulfuric Acid-Ionic Liquid | Cyclohexanone Oxime | 5/1 | 110 | 2 | Caprolactam | 99.8% | 80.1% |
| 7 | N,N-Dimethylaspartic Acid Sulfuric Acid-Ionic Liquid | Cyclohexanone Oxime | 5/1 | 110 | 2 | Caprolactam | 99.7% | 63.5% |

EXAMPLES 8-10

In Examples 8-10, according to Table 3, a toluene solvent (50 ml) and 0.01 mole of the amino acid ionic liquid were added to a 250 ml three-necked round-bottom flask, stirred by a magnetic stirrer and heated to 110° C. A determined amount of ketoxime was added, wherein the molar ratio of the ionic liquid to ketoxime was 5/1. After the reaction was performed for 2 hours, the conversion rate of the reactant and the selectivity of the product were measured by gas chromatography. The results are shown in Table 3.

TABLE 3

| Example | Ionic Liquid | Ketoxime | Molar Ratio of Ionic Liquid/ Ketoxime | Reaction Temperature (° C.) | Reaction Time (h) | Amide | Conversion Rate | Selectivity |
| --- | --- | --- | --- | --- | --- | --- | --- | --- |
| 8 | Glutamic Acid Sulfuric Acid-Ionic Liquid | Cyclohexanone Oxime | 5/1 | 110 | 2 | Caprolactam | 99.7% | 61.7% |
| 9 | N-Methylglutamic Acid Sulfuric Acid-Ionic Liquid | Cyclohexanone Oxime | 5/1 | 110 | 2 | Caprolactam | 99.8% | 96.9% |
| 10 | N,N-Dimethylglutamic Acid Sulfuric Acid-Ionic Liquid | Cyclohexanone Oxime | 5/1 | 110 | 2 | Caprolactam | 99.8% | 99.1% |

EXAMPLES 11-18

In Examples 11-18, according to Table 4, a toluene solvent (50 ml) and 0.01 mole of the amino acid ionic liquid were added to a 250 ml three-necked round-bottom flask, stirred by a magnetic stirrer and heated to 110° C. A predetermined amount of ketoxime was added. After the reaction was performed for 3 hours, the conversion rate of the reactant and the selectivity of the product were measured by gas chromatography. The results are shown in Table 4.

TABLE 4

| Example | Ionic Liquid | Ketoxime | Molar Ratio of Ionic Liquid/ Ketoxime | Reaction Temperature (° C.) | Reaction Time (h) | Amide | Conversion Rate | Selectivity |
|---|---|---|---|---|---|---|---|---|
| 11 | N,N-Dimethylglutamic Acid Sulfuric Acid-Ionic Liquid | Cyclohexanone Oxime | 5/1 | 110 | 1 | Caprolactam | 99.9% | 96.9% |
| 12 | N,N-Dimethylglutamic Acid Sulfuric Acid-Ionic Liquid | Cyclohexanone Oxime | 5/1 | 110 | 0.5 | Caprolactam | 99.8% | 97% |
| 13 | N,N-Dimethylglutamic Acid Sulfuric Acid-Ionic Liquid | Cyclohexanone Oxime | 5/2 | 110 | 0.5 | Caprolactam | 99.7% | 89.6% |
| 14 | N,N-Dimethylglutamic Acid Sulfuric Acid-Ionic Liquid | Cyclohexanone Oxime | 5/3 | 110 | 0.5 | Caprolactam | 98.9% | 78.2% |
| 15 | N,N-Dimethylglutamic Acid Sulfuric Acid-Ionic Liquid | Cyclohexanone Oxime | 5/4 | 110 | 0.5 | Caprolactam | 81.8% | 78.2% |
| 16 | N,N-Dimethylglutamic Acid Sulfuric Acid-Ionic Liquid | Cyclohexanone Oxime | 5/5 | 110 | 0.5 | Caprolactam | 61.8% | 74% |
| 17 | N,N-Dimethylglutamic Acid Sulfuric Acid-Ionic Liquid | Cyclohexanone Oxime | 5/1 | 100 | 0.5 | Caprolactam | 85.8% | 67.9% |
| 18 | N,N-Dimethylglutamic Acid Sulfuric Acid-Ionic Liquid | Cyclohexanone Oxime | 5/1 | 90 | 0.5 | Caprolactam | 55.6% | 41% |

From the above results, it is shown that the method of the present invention for preparing an amide by a ketoxime and an amino acid ionic liquid as both a reaction medium and a catalyst to catalyze the Beckman rearrangement of a ketoxime has a high conversion rate of the ketoxime and a high selectivity of the amide, wherein the conversion rate and selectivity are more preferable when the molar ratio of an ionic liquid/a ketoxime is between 5/1 and 5/2. The preferable reaction temperature and reaction time are 100 to 110° C. and 0.5 to 2 hours respectively.

In the present invention, the amino acid ionic liquids having the asymmetric property are used as catalysts and reaction media to prepare amides by catalyzing the Beckman rearrangement of ketoximes. The reaction system of the present invention is simple, such that no additional cocatalysts are required and no by-products are produced, thereby eliminating environmental pollution and saving energy. Thus, the present invention has a promising prospect in industrial applications.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing an amide, comprising the steps of:
catalyzing Beckman rearrangement of a ketoxime to produce an amide in the presence of a catalyst,
wherein the catalyst is an N-substituted amino acid ionic liquid having a cation represented by the following formula (I) and one or more anions selected from the group consisting of inorganic acid ions, organic acid ions and a combination thereof:

wherein $R_1$ is hydrogen, cycloimino, or $C_1$-$C_8$alkyl, in which the $C_1$-$C_8$alkyl is unsubstituted or substituted by a substituent selected from the group consisting of hydroxyl (—OH), carboxyl (—COOH), guanidino ($NH_2C(=NH)NH$—), amino (—$NH_2$), amido (RCONH—), hydroxyphenyl, $C_1$-$C_8$alkylthio, thiol (—SH), $C_6$-$C_{10}$aryl and 5- to 10-membered heteroaryl; and $R_2$ and $R_3$ are independently hydrogen or $C_1$-$C_8$alkyl, in which the $C_1$-$C_8$alkyl is unsubstituted or substituted by a substituent selected from the group consisting of carboxyl (—COOH), sulfo (—$SO_3H$), chlorosulfinyl (ClSO—), ester group (—COOR, wherein R is $C_1$-$C_8$alkyl), oxo (=O) and $C_6$-$C_{10}$aryl, provided that $R_2$ and $R_3$ are not hydrogen concurrently, wherein the numbers of the anion and the cation are such that the N-substituted amino acid ionic liquid is electroneutral.

2. The method of claim 1, wherein the $R_1$ is $C_1$-$C_8$alkyl substituted by carboxyl (—COOH), guanidino ($NH_2C(=NH)NH$—), amino (—$NH_2$), amido (RCONH—), or hydroxyphenyl, and the $R_2$ and $R_3$ are independently $C_1$-$C_8$alkyl.

3. The method of claim 1, wherein the anion is selected from the group consisting of sulfate, methylsulfonato, trifluoroacetato and a combination thereof.

4. The method of claim 3, wherein the anion is sulfate.

5. The method of claim 1, wherein the N-substituted amino acid ionic liquid is an amino acid sulfuric acid-ionic liquid selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof.

6. The method of claim 5, wherein the ketoxime is selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime.

7. The method of claim 6, wherein the N-substituted amino acid ionic liquid is an N,N-dimethylglutamic acid sulfuric acid-ionic liquid, and the ketoxime is cyclohexanone oxime.

8. The method of claim 1, wherein a molar ratio of the N-substituted amino acid ionic liquid to the ketoxime is between 1:10 and 10:1.

9. The method of claim 8, wherein the molar ratio of the N-substituted amino acid ionic liquid to the ketoxime is between 1:5 and 5:1.

10. The method of claim 1, wherein the reaction is performed at a temperature in a range from 60 to 150° C.

11. The method of claim 9, wherein the reaction is performed at a temperature in a range from 90 to 130° C.

12. The method of claim 1, wherein the reaction is performed for 0.1 to 10 hours.

13. The method of claim 12, wherein the reaction is performed for 0.5 to 3 hours.

14. The method of claim 1, further comprising conducting the Beckman rearrangement in the presence of an organic solvent.

15. The method of claim 1, wherein the ketoxime is selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime.

16. The method of claim 15, wherein the N-substituted amino acid ionic liquid is an N,N-dimethylglutamic acid sulfuric acid-ionic liquid, and the ketoxime is cyclohexanone oxime.

* * * * *